United States Patent [19]
Wollinsky et al.

[11] Patent Number: 5,462,667
[45] Date of Patent: Oct. 31, 1995

[54] FILTER FOR LIQUOR FILTRATION

[75] Inventors: Kurt H. Wollinsky, Illerkirchberg; Michael W. K. Saefkow, Langen, both of Germany

[73] Assignee: Pall Corporation, East Hills, N.Y.

[21] Appl. No.: 313,535

[22] Filed: Sep. 27, 1994

Related U.S. Application Data

[63] Continuation of Ser. No. 30,375, filed as PCT/EP91/01864, Sep. 30, 1991, abandoned.

[30] Foreign Application Priority Data

Oct. 5, 1990 [EP] European Pat. Off. .............. 90119187

[51] Int. Cl.$^6$ .............. B01D 61/00; B01D 29/00
[52] U.S. Cl. .............. 210/645; 210/651; 210/653; 210/654; 210/500.37; 210/500.38; 210/490; 210/321.72; 428/308.4
[58] Field of Search .............. 210/645, 490, 210/500.27, 500.21, 500.37, 500.38, 651, 321.72, 653, 654; 264/41; 428/308.4

[56] References Cited

U.S. PATENT DOCUMENTS

| | | |
|---|---|---|
| 3,591,493 | 7/1971 | Zeineh . |
| 3,876,738 | 4/1975 | Marinaccio et al. .............. 264/41 |
| 4,340,479 | 7/1982 | Pall .............. 210/490 |
| 4,473,474 | 9/1984 | Ostreicher et al. .............. 210/636 |
| 4,673,504 | 6/1987 | Ostreicher et al. .............. 210/500.38 |
| 4,702,840 | 10/1987 | Degen et al. .............. 210/638 |
| 4,707,266 | 11/1987 | Degen et al. .............. 210/638 |
| 4,708,803 | 11/1987 | Ostreicher et al. .............. 210/650 |
| 4,915,839 | 4/1990 | Marinaccio et al. .............. 210/500.38 |
| 5,120,502 | 6/1992 | Gordon et al. .............. 210/321.72 |
| 5,334,315 | 8/1994 | Matkovich et al. .............. 210/641 |

FOREIGN PATENT DOCUMENTS

| | | |
|---|---|---|
| 0080680 | 6/1983 | European Pat. Off. . |
| 0098392 | 1/1984 | European Pat. Off. . |
| 92/50864 | 4/1992 | WIPO . |
| 9213501 | 8/1992 | WIPO . |

OTHER PUBLICATIONS

Mochida et al., "Pyrogenic factor appearing . . . of febrile rabbits", Chemical Abstracts, vol. 82, No. 17, Apr. 28, 1975, p. 116, abstract 107252d.
Pagano et al., "Cerebrospinal fluid procoagulant . . . by myelolymphoproliferative diseases", Biological Abstracts, vol. 83, No. 5, 1987, abstract 46268.
Pagano et al., "Spinal fluid procoagulant . . . with intrathecal methotrexate", Biological Abstracts, vol. 84, No. 2, 1987, abstract 16637.
Rotbart et al., "RNA target loss . . . a quantitative study", Molecular and Cellular Probes, vol. 1, No. 4, Dec. 1987, pp. 347–358.
"Plasmapheresis and acute Guillain–Barré Syndrome", Neurology, 35, pp. 1096–1104, Aug. 1985.
Nathan, "Secretory Products of Macrophages", J. Clin. Invest., 79, pp. 319–326, Feb. 1987.
Greuner et al, "Prediction . . . Guillain–Barré Syndrome", Arch. Neurol., 44, pp. 295–298, Mar. 1987.
'Pall' Intravenous Set Saver, Pall Posidyne ELD96 Set Saver Filter, Brochure, Pall Biomedical Ltd., 1986.
Hülser et al, "Blockierende Wirkung von Guillain–Barre . . ., Deutsche Gesellschaft . . . Neurologie", Sep. 29, 1989 w/Eng. translation.
Wollinsky et al, "Liquorpherese bei akutem . . . Guillain–Barre . . ., Deutsche Gesellschaft . . . Neurologie", Sep. 29, 1989 w/Eng. translation.
Wollinsky et al, "Liquorpherese . . . Guillain–Barre Syndroms", Der Anaesthesist, Abstracts, Sep. 12–16, 1989 w/Eng. translation.

(List continued on next page.)

Primary Examiner—Ana M. Fortuna
Attorney, Agent, or Firm—Leydig, Voit & Mayer

[57] ABSTRACT

A filter and process of using the filter for the filtration of liquor cerebrospinalis, the filter has a membrane filter layer having a pore size of from 0.04–0.45 μm a thickness of 0.1 to 1 mm, a geometric surface area of from 15–300 cm2, and a separation capacity of at least 500 μg.

39 Claims, 1 Drawing Sheet

OTHER PUBLICATIONS

Hulser et al, Liquorpheresis elim. . . . (Guillain–Barre–Syndrome), Eur Arch Psych Clin Neur (1991) 241: 69–72.

Wollinsky et al., Liquorpheresis . . .(Guillain–Barre Syndrome), Eur Arch Psych Clin Neur (1991) 241: 73–76.

Ferner et al, "Management of Guillain–Barré Syndrome" Brit. J. Hospital Med., 12, p. 525–530.

Wietholter et al. "Electrophysiological follow-up . . . in rats", J. of Neurological Sciences, 83, pp. 1–14, 1988.

FILTER FOR LIQUOR FILTRATION

This application is a continuation of application Ser. No. 08/030,375, now abandoned, filed as PCT/EP91/01864, Sep. 30, 1991.

The invention relates to a filter for the filtration of liquor cerebrospinalis, in particular for the treatment of neurologic diseases which are accompanied by inflammable processes (neuritides, for example polyradiculitis, radiculoneuritis or Guillain Barré syndrome (GBS), or which represent non-inflammable processes (neuropathies) as well as intoxications of the liquor (such as diphtheria or rabies) or infections by bacteria (for example borreliose) or viruses (for example virus encephalitis, polio), which manifest causally or symptomatically in the nervous system.

GBS, for example, is an ascending motoric and nerve-related paralysis and ascending nerve paralysis, respectively, including the lower brain nerves (which first extend to the extremities so that the patient cannot walk any more and becomes bed ridden, respectively, and can lead to a total paralysis of all muscles so that a long-term aspirator treatment of the patient is required. A degeneration of nerves with long-time defects is possible.

The aforesaid diseases cause a change of the liquor composition. The reasons for these symptoms are still unclear, and in particular a causality between the changed liquor composition and the disease symptoms has not been established. The therapy of the Guillain Barré syndrome consists in the therapeutic plasmapheresis, i.e., a (partial) plasma exchange, wherein, after blood withdrawal from the patient, a mechanical separation of corpuscular elements and plasma, for example by centrifuging, occurs. The corpuscular constituents, after total or partial volume replacement of the withdrawn plasma, are resuspended in the plasma substitute and reinfused into the patient. With numerous patients, however, the method of plasmapheresis produces little or no improvement in the disease symptoms.

It has now been found that the latter causes a substantial improvement in the condition of the patient, and complete alleviation of symptoms can be achieved if the liquor of this patent is subjected to a filtration through a specific filter.

Accordingly, the invention relates to a filter for use in a method for the filtration of liquor cerebrospinalis, which filter is characterized by a membrane filter layer having a pore width of from 0.04 to 0.45 µm and a thickness of from 0.1 to 1 mm, wherein said filter has a geometric surface area of from 50 to 300 cm$^2$ and a pyrogen separation capacity of at least 500 µg.

The pyrogen separation capacity, given in µg, means that the filter withholds the stated amount of pyrogen, based on a standard *E. coli* endotoxin in a concentration range of between 0.6 and 6.9 ng/ml in the starting material, wherein the concentration in the filtrate is below the limit of the LAL test (limulus-amoebocytes-lysate test) (about 0.006 ng/mi).

Pyrogenic compounds (pyrogens) (fever-generating compounds) are primarily heat-resistant, dialyzable compounds of a pathogenic and pathogenic bacteria, fungi or viruses which, when administered to man in extremely small amounts (<1 µg/kg) cause shivers and an increase in temperature (fever). In terms of their chemical character, pyrogenic compounds are mainly oligo, poly- and lipopolysaccharides or polypeptides, wherein the strongest effective pyrogenic compounds are those of Gram negative bacteria.

Pyrogenic compounds are of importance as impurities in injection or infusion solutions from which they must be removed by means of so-called bacteria filters. By definition these bacteria filters are microporous materials by means of which bacteria can be removed from gases or liquids by sieve or adsorption effect, for example glass, membrane or sieve filters (cf. Roche Lexikon Medizin, 1st Edition 1984, page 135). The determination of the pyrogen separation capacity occurs by use of a standard pyrogenic compound, i.e., with an *E. coli* endotoxin, wherein the efficiency of the separation is checked with the rabbit test or the LAL test (cf. Pharm. Ind. 47 (1985) 407–411). Commercial bacteria filters which are used as infusion filters for the protection of patients have pyrogen separation capacities below 100 µg, and a geometric filter area of about 10 cm$^2$.

The use of the filter according to the invention is a method whereby the filtering of liquor cerebrospinalis can be carried out in a very simple manner. In practice it has been found that such a simple and convenient method is one whereby after inserting in the patient an intrathecal catheter comprising two three-way cocks, a 10 ml syringe and the liquor filter, a closed system is installed. Then, 10–40 ml liquor each are manually withdrawn and replaced after passage through the filter. With this method 6 GBS patients were treated, 4 having an acute and 2 having a chronic history. With 3 of the patients intensive plasmapheresis carried out before had been without effect on their symptoms. In 1 to 2 daily treatments for up to 5 days a maximum of 150 ml liquor each was filtrated. The method was tolerated well by all patients and without complications. Headaches occurred only fleetingly and were not as intense as is usually observed with lumbar punctures. With all patients there could be observed, timely related to the liquor filtration, and sometimes during the treatment, pronounced, or sometimes a significant improvement in the clinical symptoms. With acute patients and patients treated in early stages of GBS the improvement was more pronounced and faster than in the case of chronic patients.

A filtration of the liquor can also be indicated with other symptoms which are accompanied by a change of the liquor, for example with multiple Sclerosis or ALS.

The membrane filter layer of the filter of the invention has a pore size of from 0.04 to 0.45 µm, preferably from 0.1 to 0.3 µm and most preferably from 0.1 to 0.2 µm. Membrane filter layers having such a pore size are known per se and are used in bacteria filters for the administration of infusion solutions, wherein membranes having a pore size below 0.1 µm are also used as virus filters. The common bacteria filters are, however, not suitable in accordance with the invention since when using same for liquor filtration, no significant change is achieved. In addition, because of the uncertain causes of the Guillain Barré syndrome, a significant improvement of the symptoms of the disease could not be expected with the claimed filter.

The filter of the invention has a pyrogen separation capacity of at least 500 µg, for example at least 600 or 700 µg, and preferably of at least 1000 µg, wherein a range of from 1000 to 2000 µg is especially preferred.

The membrane filter layer has a layer thickness of from 0.1 to 1 mm, wherein said filter has a geometric surface area of from 50 to 300 cm$^2$.

Within the said ranges of from 0.04 to 0.45 µm for the pore width, 50 to 300 cm$^2$ for the geometric surface area and 0.1 to 1 mm for the thickness of the membrane filter layer, a correlation is made so that the required pyrogen separation capacity of at least 500 µg and a flow rate sufficient for practical use is achieved. In general the flow rate is about proportional to the pore width and the surface area and about inversely proportional to the layer thickness, whereas the separation capacity is proportional to the layer thickness and to the geometric surface area.

A further parameter for controlling the pyrogen separation capacity and the flow rate is the pore volume, expressed as percentage of the pore volume based on the total volume, wherein within certain limits both the separation capacity and the flux rate are about proportional to the pore volume. The pore volume should be as high as possible in order to be able to keep the filter as small as possible. The pore volume, however, has upper limits. In practice the pore volume is generally 50–90%, wherein for the afore-stated reason the higher values are preferred. As material for the membrane filter layer all inert polymeric materials are convenient from which membranes with the stated pore ranges can be made according to known methods. Examples for suitable materials are plastics inert against body fluids, such as polyolefines, for example. polyethylene or polypropylene, polyamides, for example nylon 6,6 or polycaprolactame, polyester or polyvinylidene fluoride.

In a preferred embodiment the membrane filter layer is a charge-modified membrane for the reason that the separation capacity can be achieved moved easily in this way. Charge-modified membranes both with positive zeta potential and with negative zeta potential are commercially available. The preferred charge-modified membranes are those which have been made by adding a charge modifying agent to the dope solution from which the membrane is cast.

The charge-modified membranes having a positive zeta potential are also designated as cationic membranes. A suitable membrane is, for example, of a polyamide, for example nylon 6,6, wherein the charge modification of the membrane is accomplished by adding a heat-settable polymer carrying quaternary ammonium groups, to the polymer dope. Since the positive charge of these membranes stems from the presence of the quaternary ammonium groups, they maintain their positive charge in acidic, neutral and alkaline pH range.

The charge-modified membranes having a negative zeta potential are also designated as anionic membranes. Sources for the negative charge are ionizable functional polar groups, such as carboxylic acid groups, sulfonic acid groups, phenolic amino groups, sulfhydryl-, sulfide-, thiocarbonyl-, phosphine-, phosphoryl- or thiophosphoryl groups. Carboxyl groups are preferred.

In a further preferred embodiment the filter of the invention is a composite filter, wherein the filter comprises a second membrane filter layer having a pore size in the range of 0.1 to 5 µm and a thickness of 0.1 to 1 min. In this case the first membrane filter layer can be made very thin, since its function remains only in separating bacteria and viruses, respectively, whereas in the second (preceding) layer the major amount of deliterious constituents has already occurred though adsorption. In this embodiment the essential part of the separation capacity is thus provided by the preceding second layer. The primary importance of the second filter layer is in the adsorption capacity rather than in the pore size, and for this reason a larger pore size, for example of 0.8 µm or 1.2 µm or up to 5 µm is suitable as well. The smaller pore size yields, however, better results with the second layer as well, and for this reason a pore size of from 0.1 to 0.45 µm is preferred.

The thickness of the second filter layer is from 0.1 to 1 min. With increasing pore size (and with increasing pore volume), caused by the higher flow rate, the layer thickness can be increased which, on the other hand, allows a change in the geometric surface area of the filter in the range of from 15 to 300 $cm^2$ to smaller values while maintaining the minimum pyrogen separation capacity of 500 µg.

Thus the filter of the invention is one-layered or multi-layered. With the one-layered embodiment the single membrane filter layer is preferably a charge-modified membrane such as described hereinbefore.

With the multi-layered embodiment the composite filter consists of at least two layers, wherein preferably the second (preceding) filter layer is a charge-modified membrane. In a specific embodiment of this composite filter the first filter layer is a charge-neutral membrane, for example from nylon 6,6, and the second filter layer is a charge-modified membrane, wherein the charge can be either positive or negative (positive or negative zeta potential). In a further specific embodiment of a two-layered filter the first layer is a positively charge-modified membrane and the second (preceding) layer is a negatively charge-modified membrane. In a further specific embodiment of a three-layered filter the second layer is a positively charge-modified membrane and the third layer is a negatively charge-modified membrane.

For practical use the filter of the invention, irrespective of the number and kind of its layers, has one or more supporting or carrier layers which impart mechanical strength to the filter, without changing its use properties. Furthermore, for practical use the filter is preferably arranged in a filter housing with corresponding connections, wherein the aforesaid supporting layers can also be integrated into said filter housing.

In a further preferred embodiment the filter of the invention is equipped with a means of venting. It has been found that gas bubbles can develop during the operation of the liquor filter, which gas bubbles can lead to a blocking of the filter. The venting enables these gas bubbles to escape from the filter housing while maintaining sterility. A suitable venting is, for example, a usual venting valve. Preferably this purpose is achieved by a venting membrane which is a hydrophobic membrane having a pore size such that leaking of liquor liquid is prevented but gas bubbles can pass through at the filtration pressure. The venting membrane is arranged at the intake side of the filter housing, i.e., on that side at which the liquor to be filtered enters the filter housing.

BRIEF DESCRIPTION OF THE FIGURES

The following drawings illustrate the invention, wherein

FIG. 1 a one-layered membrane filter layer for a liquor filter of the invention, FIG. 2 a two-layered embodiment, FIG. 3 also a two-layered embodiment, and FIG. 4 a three-layered embodiment.

Only the respective layers are shown without supporting layers and housing.

DETAILED DESCRIPTION OF THE INVENTION

Figure 1:
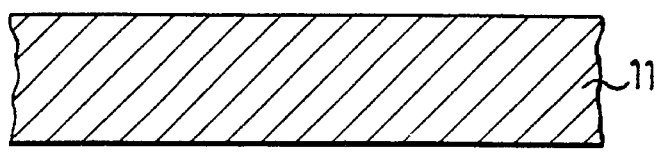
FIGS. 1–4 show, in schematic presentation, one-layered and multi-layered embodiments of liquor filters of the invention as follows.

FIG. 1 shows a membrane filter layer 11 having a layer thickness of 0.2 mm and a pore size of 0.2 µm. The material is nylon-6,6, wherein the membrane has been charge-modified by the introduction of quaternary ammonium groups so that a positive zeta potential is prevailing. Similar membranes are commercially available from, for example, Pall Corporation under its trademark Posidyne®.

The above membrane filter layer is used to make a liquor filter which, at a geometric surface area of the filter of 160 $cm^2$ has a pyrogen separation capacity of 560 µg.

Figure 2:
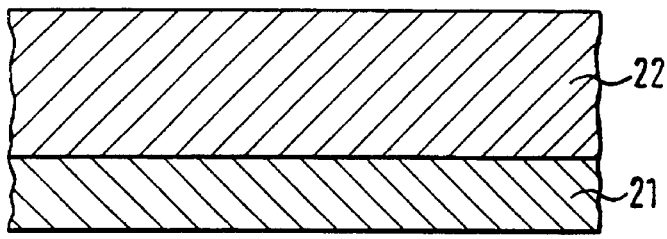

FIG. 2 shows a two-layered embodiment. The first layer 21 is of nylon-6,6 and has a thickness of 0.1 mm and a pore size of 0.04 µm. This first layer 21 is preceded by a second layer 22 of the Posidyne® material from FIG. 1, layer thickness 0.2 mm, pore size 0.2 µm.

At a geometric surface area of 160 cm² a filter made therefrom has a pyrogen separation capacity of 560 µg. Because of the pore size of 0.04 µm for the first layer 21 the composite filter is m-retentive.

Figure 3:
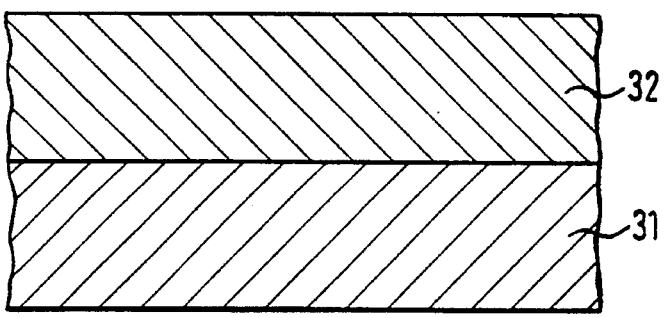

In FIG. 3 the first membrane filter layer 31 is of Posidyne® having a thickness of 0.2 mm and a pore size of 0.2 µm. The second layer 32 is a negatively charge-modified membrane, i.e. a membrane having a negative zeta potential. Such membranes are commercially available from, for example, Pall Corporation under its trademark Carboxydyne®. The second layer 32 has a thickness of 0.2 mm and a pore size of 0.2 µm.

A liquor filter made from the aforesaid composite material shows a s pyrogen separation capacity of 560 µg at a geometric surface area of 160 cm².

Figure 4:
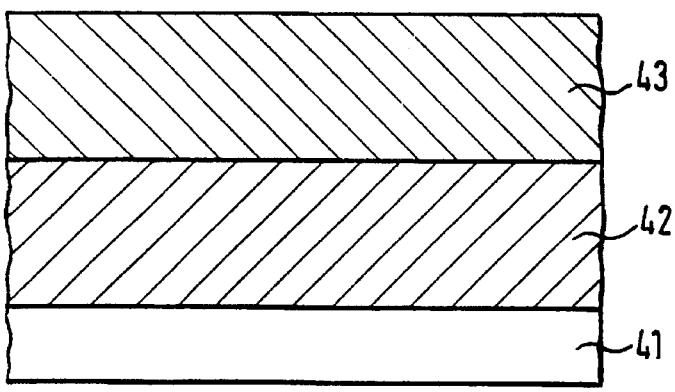

In FIG. 4 the first layer 41 has a thickness of 0.1 mm, a pore size of 0.04 µm and is of nylon-6,6. This first layer 41 takes care of the virus retention similar to the composite filter of FIG. 2.

The second layer 42 is a Posidyne® membrane having a thickness of 0.2 mm and a pore size of 0.2 µm.

The third layer 43 has a thickness of 0.2 mm, a pore size of 0.04 µm and is a Carboxydyne® membrane.

A liquor filter made from the aforesaid composite material shows a pyrogen separation capacity of 560 µg at a geometric surface area of 160 cm².

We claim:

1. A filter for use in a process for the filtration of liquor cerebrospinalis, comprising a membrane filter layer having a pore size of 0.04 to 0.45 µm and a layer thickness of from 0.1 to 1 mm, wherein said filter has a geometric surface area of from 50 to 300 cm², a pyrogen separation capacity of at least 500 µg and a pore volume from 50 to 90%.

2. The filter of claim 1 wherein the membrane filter layer has a pore size of from 0.1 to 0.3 µm.

3. The filter of claim 2 wherein the membrane filter layer has a pore size of from 0.1 to 0.2 µm.

4. The filter of any of claim 2 wherein said membrane filter layer is a charge-modified membrane.

5. The filter of claim 1 wherein the membrane filter layer has a pyrogen separation capacity of from 1000 to 2000 µg.

6. The filter of claim 1 wherein the membrane filter layer comprises a polyamide.

7. The filter of claim 1 comprising a composite filter, wherein the membrane layer comprises a first membrane filter layer and is preceded by a second membrane filter layer having a pore size in the range of 0.1 to 5 µm.

8. The filter of claim 7 wherein the second membrane filter layer has a pore size of from 0.1 to 0.45 µm.

9. The filter of claim 7 wherein the second membrane filter layer comprises a charge-modified membrane having a positive zeta potential.

10. The filter of claim 9 wherein the first membrane filter layer has a pore size of from 0.04 to 0.01 µm.

11. The filter of claim 7 wherein the first membrane filter layer comprises a charge-modified membrane having a positive zeta potential, and the second membrane filter layer comprises a charge-modified membrane having a negative zeta potential.

12. The filter of claim 7 wherein the second membrane filter layer comprises a charge-modified membrane having a positive zeta potential, said filter further comprising a third membrane filter layer, wherein said third membrane layer is a charge-modified membrane having a negative zeta potential.

13. The filter of claim 12 wherein the first membrane filter layer has a pore size of from 0.04 to 0.1 µm.

14. The filter of claim 1 having one or more supporting layers providing mechanical strength to the filter without changing the filtering properties.

15. The filter of claim 1 having a filter housing with connection pieces for retaining the filter disposed within the housing.

16. The filter of claim 15 having a venting means at the intake side of the filter housing.

17. The filter of claim 10 having a pore size from 0.1 to 0.04 µm.

18. The filter of claim 1 having a pyrogen separation capacity of at least 600 µg.

19. The filter of claim 18 wherein said membrane filter layer is a charge-modified membrane.

20. The filter of claim 18 wherein said membrane-filter layer comprises a charge-modified membrane having a positive zeta potential.

21. The filter of claim 20 wherein the membrane filter layer has a pore size of from 0.04 to 0.3 µm.

22. The filter of claim 1 having a pyrogen separation capacity of at least 700 µg.

23. The filter of claim 1 comprising a composite filter, wherein the membrane layer comprises a first membrane filter layer and is preceded by a second membrane filter layer, wherein the first membrane filter layer comprises a charge-modified membrane having a positive zeta potential and the second membrane filter layer comprises a charge-modified membrane having a negative zeta potential.

24. A method for the filtration of liquor cerebrospinalis comprising passing liquor cerebrospinalis through a filter comprising a membrane layer having a pore size of 0.04 to 0.45 µm and a layer thickness of from 0.1 to 1 mm, wherein said filter has a geometric surface area of from 50 to 300 cm², a pyrogen separation capacity of at least 500 µg, and a pore volume from 50 to 90%.

25. The method of claim 24, wherein the membrane filter layer has a pore size of from 0.1 to 0.3 µm.

26. The method of claim 25 wherein the membrane filter layer has a pore size of from 0.1 to 0.2 µm.

27. The method of claim 24, wherein the membrane filter layer has a pyrogen separation capacity of from 1000 to 2000 µg.

28. The method of claim 24, wherein the membrane filter layer comprises a polyamide.

29. The method of claim 24, wherein the filter comprises a composite filter, wherein the membrane filter layer comprises a first membrane filter layer and is preceded by a second membrane filter layer having a pore size in the range of 0.1 to 5 µm.

30. The method of claim 29 wherein the second membrane filter layer has a pore size of from 0.1 to 0.45 µm.

31. The method of claim 29 wherein the second membrane filter layer comprises a charge-modified membrane having a positive zeta potential.

32. The method of claim 29 wherein the first membrane filter layer comprises a charge-modified membrane having a positive zeta potential, and the second membrane filter layer comprises a charge-modified membrane having a negative zeta potential.

33. The method of claim 29 wherein the second membrane filter layer comprises a charge-modified membrane having a positive zeta potential, said filter further comprising a third membrane filter layer, wherein said third membrane layer comprises a charge-modified membrane having a negative zeta potential.

34. The method of claim 32 wherein the first membrane filter layer has a pore size of from 0.04 to 0.1 µm.

35. The method of claim 24, wherein the filter has one or more supporting layers providing mechanical strength to the filter without changing the filtering properties.

36. The method of claim 24, wherein said filter has a pore size from 0.1 to 0.04 µm.

37. The method of claim 24 wherein the filter has a pyrogen separation capacity of at least 600 µg.

38. The method of claim 24 wherein the filter has a pyrogen separation capacity of at least 700 µg.

39. The method of claim 24 wherein the membrane filter layer comprises a charge-modified membrane.

* * * * *

UNITED STATES PATENT AND TRADEMARK OFFICE
CERTIFICATE OF CORRECTION

PATENT NO. : 5,462,667
DATED : October 31, 1995
INVENTOR(S) : Wollinsky et al.

It is certified that error appears in the above-indentified patent and that said Letters Patent is hereby corrected as shown below:

Column 5, Line 44, after "filter" delete --of any--;

Line 60, change "0.01" to --0.1--;

Column 6, Line 15, change "10" to --1--;

Line 21, delete -- - --

Signed and Sealed this

Fourth Day of June, 1996

Attest:

BRUCE LEHMAN

*Attesting Officer*    *Commissioner of Patents and Trademarks*